(12) United States Patent
Yamaoka et al.

(10) Patent No.: US 9,206,398 B2
(45) Date of Patent: Dec. 8, 2015

(54) METHOD FOR PURIFYING PROTEIN AND GLUCOSE DEHYDROGENASE

(75) Inventors: Hideaki Yamaoka, Kyoto (JP); Keisuke Kurosaka, Uji (JP); Shido Kawase, Uji (JP)

(73) Assignee: ARKRAY, Inc., Kyoto (JP)

( * ) Notice: Subject to any disclaimer, the term of this patent is extended or adjusted under 35 U.S.C. 154(b) by 308 days.

(21) Appl. No.: 13/308,994

(22) Filed: Dec. 1, 2011

(65) Prior Publication Data

US 2012/0309072 A1 Dec. 6, 2012

Related U.S. Application Data

(62) Division of application No. 10/526,026, filed on Aug. 11, 2005, now abandoned.

(30) Foreign Application Priority Data

Aug. 30, 2002 (JP) ................................. 2002-253742

(51) Int. Cl.
| | |
|---|---|
| C12N 9/04 | (2006.01) |
| C12P 21/06 | (2006.01) |
| C07K 1/20 | (2006.01) |
| C07K 1/18 | (2006.01) |
| C12N 9/02 | (2006.01) |

(52) U.S. Cl.
CPC ................ C12N 9/0006 (2013.01); C07K 1/18 (2013.01); C07K 1/20 (2013.01); C12N 9/0004 (2013.01)

(58) Field of Classification Search
CPC ....... C07K 1/18; C12N 9/0006; C12N 9/0004
USPC ........................................... 435/190, 26, 189
See application file for complete search history.

(56) References Cited

U.S. PATENT DOCUMENTS

| | | | |
|---|---|---|---|
| 5,126,256 A | 6/1992 | Ebeling et al. | |
| 5,250,415 A | 10/1993 | Ebeling et al. | |
| 5,939,536 A | 8/1999 | O'Riordan et al. | |
| 7,741,090 B2 | 6/2010 | Sode | |
| 2004/0023330 A1* | 2/2004 | Sode | 435/69.1 |

FOREIGN PATENT DOCUMENTS

| | | |
|---|---|---|
| EP | 0290768 A2 | 11/1988 |
| JP | 57-068138 | 4/1982 |
| WO | 02/36779 A1 | 5/2002 |

OTHER PUBLICATIONS

K.Inose et al.; "Cloning and expression of the gene encoding catalytic subunit of thermostable glucose dehydrogenase from *Burkholderia cepacia* in *Escherichia coli*"; Biochemical et Biophysics Acta, pp. 133-138, Apr. 15, 2002.
Y. Shimomura et al., Purification of teh Iron—Sulfur Protein, Ubiquinone-Binding Protein, and Cytochrome c1 from a Single Source of Mitochondrial Complex III; Analytical Biochemistry, vol. 153, pp. 126-131, 1986.
Y.Imai; The Use of 8-Aminooctyl Sepharose for the Separation of Some Components of the Hepatic Microsomal Electron Transfer System; J. Biochem, vol. 80, pp. 267-276, 1976.
P.M. Strasberg et al.; "Purification of gluccosylceramidase by affinity chromatography"; Can J. Biochem. vol. 60, pp. 1025-1031, 1982.
R. Palfree et al.; "Biochemical Characterization of teh Murine Activated Lymphocyte Alloantigen LY-6E.1 Controlled by the LY-6 Locus"; The Journal of Immunology, vol. 136, No. 2, Jan. 15, 1986, pp. 594-600.
Supplementary European Search Report; EP 03794088; May 16, 2007.

* cited by examiner

*Primary Examiner* — Tekchand Saidha
*Assistant Examiner* — Md. Younus Meah
(74) *Attorney, Agent, or Firm* — Studebaker & Brackett PC (57) ABSTRACT

The present invention relates to a method for purifying target protein which contains electron transfer protein, from a protein solution containing the target protein, by means of liquid chromatography. The liquid chromatography is performed as follows: First, the protein solution is introduced into a column which is filled with a packing agent, thereby causing the packing agent to bond to the target protein. Then, impurities are removed, and then the target protein is eluted from the packing agent in an eluent which contains a hydroxy-cholate. An example of the target protein is glucose dehydrogenase which contains a protein having glucose dehydrogenation activity. The liquid chromatography is performed as a combination of hydrophobic chromatography and anion exchange chromatography.

17 Claims, 2 Drawing Sheets

METHOD FOR PURIFYING PROTEIN AND GLUCOSE DEHYDROGENASE

TECHNICAL FIELD

The present invention relates to a method for purifying protein by using liquid chromatography. The method is used, for example, when purifying glucose dehydrogenase which is bonded to electron transfer protein.

BACKGROUND ART

Development efforts have been made in many different fields of industry for biosensors incorporating an enzyme which makes a specific reaction with a specific substrate. A representative example of such biosensors is a glucose sensor utilized mainly in the field of medical care.

The glucose sensor establishes a reaction system which includes an enzyme and an electron transfer material. When using the glucose sensor, an amperometric method for example is employed to quantitate glucose. The enzyme is provided by e.g. glucose oxidase (GOD) and glucose dehydrogenase (GDH).

GOD has high substrate specificity to glucose, high thermal stability, and is less expensive than other enzymes because it can be mass-produced industrially. A shortcoming on the other hand is that reaction systems involving GOD are highly sensitive to oxygen dissolved in the sample, and so the dissolved oxygen can affect the measurement.

On the other hand, reaction systems involving GDH are not susceptible to dissolved oxygen in the sample. For this reason, reaction systems which utilize GDH allow accurate measurement of the glucose level even if the measurement is made in an environment poor in oxygen partial pressure, or if the measurement is made to a high-concentration sample which has a high oxygen demand. Shortcomings of GDH include poor thermal stability and lower substrate specificity than GOD.

Under these circumstances, efforts have been made in search for an enzyme which covers the shortcomings of both GOD and GDH. As disclosed in the International Disclosure WO02/36779, Hayade separated a new strain (*Burkholderia cepacia* KS1) from soil near a hot spring, and obtained a new GDH from the strain. This GDH included α, β, γ subunits (hereinafter called "CyGDH"), had a high rate of reaction with electron transfer materials, and sufficient thermal stability, and so was suitable for use in glucose sensors.

When utilizing CyGDH in glucose sensors, CyGDH must be purified from an enzyme solution which contains CyGDH. Enzyme is usually purified by means of liquid chromatography, so the inventor et al. of the present invention followed a common method of hydrophobic chromatography and anion exchange chromatography in an attempt to process the enzyme solution. However, it was not possible to purify CyGDH to a high level of purification, as SDS-PAGE examinations revealed that the obtained enzyme solution contained a number of different proteins in addition to α, β, γ subunits.

DISCLOSURE OF THE INVENTION

The present invention aims at providing a new method for purifying a protein.

A first aspect of the present invention provides a method for purifying a target protein from a protein solution which contains the target protein, by using liquid chromatography. The liquid chromatography includes: a first step of introducing the protein solution into a column which is filled with a packing agent and causing the packing agent to hold the target protein; and a second step of eluting the target protein by using an eluent which contains a hydroxy-cholate.

It should be noted here that in the present specification, that the term "liquid chromatography" refers, unless otherwise specified, to both of a column method in which the purification is made in a flow (continuously), and a batch method of purifying protein. An example of the batch method is placing a packing agent and the protein solution together in a column to cause the packing agent to bind the target protein, then separating the packing agent, and then bringing the packing agent in contact with the eluent thereby separating and collecting the target agent from the packing agent.

An example of the target protein, which is the object of the purification, is a protein which contains electron transfer protein. A typical example of the target protein is glucose dehydrogenase which contains an electron transfer protein and a protein that has glucose dehydrogenation activity.

The packing agent can be an ion-exchange gel, and the protein is purified by means of an ion-exchange chromatography. In this case, the ion-exchange gel contains a quaternary ammonium group as an ion-exchange group.

Here, the term "hydroxy-cholate" refers to salts of cholic acid which are trihydrates of cholanic acids, as well as their derivatives in a broad sense. Examples of hydroxy-cholates include cholates, glicoursodeoxycholate, tauroglicoursodeoxycholate, tauroursodeoxycholate, ursodeoxycholate, glycocholate, taurocholate, glycochenodeoxycholate, taurochenodeoxycholate, glycodeoxycholate, taurodeoxycholate, chenodeoxycholate, deoxycholate, glycolithocholate, taurolithocholate, and lithocholate. Among others, it is preferable to use a cholate such as sodium cholate.

When eluting the target protein from the packing agent, preferably, the concentration of the hydroxy-cholate in the eluent is maintained at a constant level. In this case, the concentration of the hydroxy-cholate in the eluent is preferably selected from a range of 0.5 through 2.5 wt %, and more preferably, from 0.8 through 1.2 wt %. Such a method is applied not only to the elution of the target protein in a batch process but also to the elution of the target protein in a continuous process. Alternatively, the concentration of the hydroxy-cholate in the eluent may be varied with time, in eluting the target protein. In this case, the upper limit concentration of the eluting agent should be not higher than 3 wt % for example, and more preferably not higher than 1.5 wt %, and most preferably not higher than 1 wt %. In other words, the concentration of the eluent is varied within the range of 0-3 wt % for example, more preferably within the range of 0-1.5 wt %, and most preferably within the range of 0-1.0 wt %.

The electron transfer protein has a molecule weight of e.g. approximately 43 kDa in SDS-gel electrophoresis under a reducing environment. On the other hand, the protein which has glucose dehydrogenation activity has a molecule weight of approximately 60 kDa in SDS-gel electrophoresis under a reducing environment. Glucose dehydrogenase which contains such electron transfer protein and subunits is obtainable from e.g. a microorganism belonging to the genus *Burkholderia* which is capable of producing the glucose dehydrogenase, or from a transformant thereof.

There is no specific limitation to the microorganism of the genus *Burkholderia* which is used in the present invention, as long as the microorganism is capable of producing the target enzyme. Preferably, however, *Burkholderia cepacia*, and *Burkholderia cepacia* KS1 strain (hereinafter simply called "KS1 strain") in particular, is preferred. KS1 strain was deposited as FERM BP-7306, on Sep. 25, 2000, with the International Patent Organism Depositary (IPOD), National Institute of Advanced Industrial Science and Technology (AIST) (Tsukuba Central 6, 1-1-1 Higashi, Tsukuba, Ibaraki, Japan 305-8566).

The transformant can be produced, for example, by engineering a host microorganism with a DNA from a microorganism belonging to the genus *Burkholderia* for coding the electron transfer protein and the protein active against glucose. The host microbe is preferably a microorganism belonging to the genus *Pseudomonas* (*Pseudomonas putida* in particular) or *E. coli* bacterium.

As disclosed in International Publication WO02/36779 and others, glucose dehydrogenase derived from KS1 strain contains a subunit (α subunit) and an electron transfer protein (β subunit), and γ subunit which has a molecular weight of approximately 14 kDa in the SDS gel-electrophoretic migration under reducing environment.

Hayade has confirmed that higher enzyme activity is achieved by a combination of γ subunit and α subunit than by α subunit only. Therefore, in view of enzyme activity, it is preferable to manifest γ subunit, and when engineering the DNA, γ subunit structural gene should preferably be included in an upstream region of α subunit. Then, when the transformant produces α subunit, γ subunit which has been manifested already and existing as a protein will promote efficient production of α subunit in the microorganism.

A second aspect of the present invention provides a method for purifying glucose dehydrogenase using a combination of hydrophobic chromatography and anion exchange chromatography. The hydrophobic chromatography includes: a step of causing a stationary phase to hold the glucose dehydrogenase; a step of eluting unnecessary proteins; and a step of eluting the glucose dehydrogenase by using an eluent containing a hydroxy-cholate. The anion exchange chromatography includes: a step of causing a stationary phase to hold the glucose dehydrogenase; and a step of eluting the glucose dehydrogenase by using an eluent containing a hydroxy-cholate.

In the hydrophobic chromatography, elution of the glucose dehydrogenase for example, is performed by varying the concentration of the hydroxy-cholate in the eluent with time. On the other hand, in the anion exchange chromatography, elution of the glucose dehydrogenase for example, is performed by keeping the concentration of the hydroxy-cholate in the eluent. Alternatively, the concentration of the hydroxy-cholate in the eluent may be varied with time, in eluting the target protein. In this case, the upper limit concentration of the eluting agent should be not higher than 3 wt % for example, and more preferably not higher than 1.5 wt %, and most preferably not higher than 1 wt %. In other words, the concentration of the eluent is varied within the range of 0-3 wt % for example, more preferably within the range of 0-1.5 wt %, and most preferably within the range of 0-1.0 wt %.

In the method for purifying glucose dehydrogenase according to the present invention, preferably, the anion exchange chromatography is carried out after the hydrophobic chromatography.

The glucose dehydrogenase is produced by e.g. a microorganism belonging to the genus *Burkholderia*. An example of the microorganism belonging to the genus *Burkholderia* is KS1 strain.

The glucose dehydrogenase may be made by a transformant. The transformant can be produced by engineering a host microorganism with a DNA from a microorganism belonging to the genus *Burkholderia* for coding the glucose dehydrogenase. The host microbe can be *Pseudomonas putida* or *E. coli* bacterium for example.

In the method for glucose dehydrogenase according to the present invention, preferably, the anion exchange chromatography is performed by using an ion-exchange gel which contains a quaternary ammonium group as an ion-exchange group, and the hydroxy-cholate is provided by a cholate.

BEST MODE FOR CARRYING OUT THE INVENTION

Hereinafter, methods of purifying a protein according to the present invention will be described specifically, taking an example of purifying glucose dehydrogenase (hereinafter called "GDH").

When purifying glucose dehydrogenase, first, an enzyme solution is prepared. The enzyme solution may be obtained from a microbe which produces the glucose dehydrogenase, a culture of the microbe, a transformant derived through insertion of DNA which is extracted from the microbe, or a culture of the transformant.

If GDH is inside the microbe, the enzyme solution can be obtained by first separating the microbe from the culture through filtration, centrifugation, etc., and then fragmentizing the microbe mechanically or enzymatically with e.g. lysozyme, followed as necessary, by solubilization of GDH through addition of a chelating agent such as EDTA and a surfactant. On the other hand, if GDH is outside the microbe (in the culture), the enzyme solution can be obtained by separating the microbe from the culture through filtration, centrifugation and so on.

Among microbes which produce glucose dehydrogenase, microbes of the genus *Burkholderia*, and *Burkholderia cepacia* in particular is preferably utilized. From *Burkholderia cepacia*, it is possible to obtain the enzyme solution in the form of a solubilized membrane fraction for example. In order to obtain the solubilized membrane fraction, for example, first the microbe is centrifugally separated from a culture, and the microbe is fragmentized to obtain a cell extract. The cell extract is then centrifuged, and thereafter, obtained supernatant fluid is super-centrifuged. The resulting sediment is the solubilized membrane fraction. The fragmentization of the microbe can be made in an ordinary mechanical or enzymatic method.

The transformant can be produced by first obtaining DNA which codes manifestation of e.g. α subunit (a protein having glucose dehydrogenating activity) and β subunit (electron transfer protein), and then introducing the DNA into a host microbe by using a recombinant vector.

When obtaining the DNA, first, a recombinant vector is constructed. The construction of recombinant vector can be achieved by first separating and purifying a chromosome DNA from a microbe which produces an enzyme having glucose dehydrogenation activity, preparing the chromosome DNA fragments through shredding or PCR amplification, and then binding and closing the chromosome DNA fragments with a linear expression vector.

Examples of the host microbe include E. coli and other enteric bacteria, gram-negative bacteria such as the genus pseudomonas and the genus Gluconobacter, gram-positive bacteria including the genus Bacillus such as Bacillus subtilis, yeasts such as Saccharomyces cerevisiae, and filamentous bacteria such as Aspergillus niger. Among these, E. coli bacteria and those of the genus pseudomonas (pseudomonas putida for example) are preferably used. The transformation of the microbes can be made by competent cell method through calcium treatment for the genus Escherichia. Protoplast methods can be used for the genus bacillus, KU method and KUR method for yeasts, and micromanipulation methods for filamentous bacteria. Transformation can also be made by using electropolation method.

The enzyme solution is purified by using liquid chromatography. In performing the purification through liquid chromatography, a selection is made for the type, number and combination of different types of chromatography so that a target level of purification can be achieved. Usable types of liquid chromatography include gel filtration chromatography, adsorption chromatography, ion exchange chromatography and affinity chromatography.

The liquid chromatography may be made by first having the target protein captured in the stationary phase in the column, and then supplying eluent continuously thereby eluting the target protein. Alternatively, a batch method may be used. In the batch method, for example, a column is supplied with a packing agent and a solution which contains a target protein so the packing agent will hold the target protein. Then, impurities are removed, and eluent is supplied to elute the target protein from the packing agent for collection.

The eluent is a solution which contains a hydroxy-cholate as an eluting agent. If the liquid chromatography is performed for a plurality of times before yielding the purified target protein, hydroxy-cholate is used as the eluent at least in one cycle of the liquid chromatography. In this case, preferably, hydroxy-cholate is used in the last cycle of liquid chromatography, as the eluent.

Examples of hydroxy-cholate include cholates, glicoursodeoxycholate, tauroglicoursodeoxycholate, tauroursodeoxycholate, ursodeoxycholate, glycocholate, taurocholate, glycochenodeoxycholate, taurochenodeoxycholate, glycodeoxycholate, taurodeoxycholate, chenodeoxycholate, deoxycholate, glycolithocholate, taurolithocholate and lithocholate. Among others, use of cholate, such as sodium cholate is preferred.

When bringing the eluent into contact with the packing agent, the concentration of the hydroxy-cholate in the solvent may be kept at a constant level, or the hydroxy-cholate concentration may be linearly changed with the time during the supply.

The liquid chromatography may be made directly to the enzyme solution, or may be made after the target protein in the enzyme solution has been concentrated. The concentration can be made by e.g. vacuum concentration, membrane concentration, salting-out procedure, factional precipitation using hydrophilic solvent (e.g. methanol, ethanol and acetone), heating, and isoelectric process.

The purified enzyme thus obtained, is made into a powdery product through such a process as freeze-drying, vacuum-drying and spray-drying, for distribution in the market.

EXAMPLES

Hereinafter, specific examples of the fabrication methods outlined above will be described, with demonstration that GDH can be purified more efficiently when the eluent is provided by sodium cholate than when the eluent is provided by NaCl or KCl.

<Obtainment of Enzyme Solution>

(1) Obtainment of Enzyme Solution from Burkholderia Cepacia KS1 Strain

Burkholderia cepacia KS1 strain was cultured under an aerobic condition. More specifically, the KS1 strain was cultured in 20 L of medium at 34° C. for 8 hours. The medium contained ingredients listed in Table 1, per liter.

TABLE 1

| MEDIUM COMPOSITION | |
| --- | --- |
| Polypeptone | 10 g |
| Yeast extract | 1 g |
| NaCl | 5 g |
| $KH_2PO_4$ | 2 g |
| Glucose | 5 g |
| Einol (ABLE Co., Tokyo Japan) | 0.14 g |
| Total, distilled water | 1 L |
| pH | 7.2 |

Next, the 20 L of culture medium was centrifuged at 4° C., for 10 minutes at 9000×g, to obtain approximately 250 g of microbe body. The collected microbe body was frozen, then suspended in mM phosphate buffer solution (pH6), and processed in a high-pressure homogenizer (manufactured by Rannie, Denmark) several times at a pressure of 500 bar, to fragmentize cell membrane. The cell extract obtained by cell membrane fragmentation showed a GDH activity of 60 kU. The cell extract was then centrifuged under 8000×g for 60 minutes, to remove cell solid. Further, the supernatant liquid was super-centrifuged at 10° C. under 170,000×g for an hour, to collect membrane fraction as the sediment.

The membrane fraction was dissipated in 10 mM phosphate buffer solution (pH 6), so as to have a final sodium cholate concentration of 1.5%, and KCl concentration of 0.1 M, and steered at 4° C. over a night. As a result, membrane fraction suspension which contained GDH at 30 kU was obtained. The membrane fraction suspension was super-centrifuged at 10° C. under 170,000×g for 90 minutes, to remove sediment, and to obtain GDH-containing solubilized membrane fraction (at GDH activity of 26 kU). The solubilized membrane fraction was dialyzed with 10 mM phosphate buffer solution (pH 6) for 3 nights, and the obtained insoluble matter was removed as sediment in a super centrifugation at 10° C. under 170,000×g for 90 minutes. The obtained supernatant liquid (solubilized GDH fraction) contained GDH which showed an activity of 28 kU and a specific activity of 6.8 U/mg.

(2) Obtainment of Crude Enzyme Solution from Transformants

For purification to be made in Examples and Comparative Examples hereafter, crude enzyme solution was obtained from each of two kinds of transformant each derived from a different host.

In the production of the transformants, first, DNA which includes sequences for coding manifestation of α, β and γ subunits was obtained from KS1 strain according to a common method.

Next, the obtained DNA was inserted into a vector plasmid, to produce a GDH expression plasmid, which was introduced into host microbes, to make transformants.

The hosts were provided by *Pseudomonas putida* KT2440 strain (ATCC 47054) and *E. coli* bacterium BL21 strain.

When the host was provided by *Pseudomonas putida* KT2440 strain, RSF1010 was used as the vector plasmid for inserting the GDH gene. When the host was provided by *E. coli* bacterium BL21 strain, pTrc99A was used as the vector plasmid. When the *E. coli* bacterium was used as the host, Cytochrome C maturation (ccm) gene cluster was always inserted. First, DNA which contained sequences for coding *E. coli* bacterium ccm gene cluster was obtained from JM109 strain by using a common method, and inserted into the vector plasmid, to produce ccm expression plasmid. The vector plasmid employed in this step was pBBR122. Next, transformation was made by inserting the ccm expression plasmid into the host *E. coli* bacterium which had already engineered with the GDH expression plasmid.

Each transformant was cultured separately from each other.

*Pseudomonas putida* transformant was cultured under normal aerobic conditions, in 20 L of culture solution. Composition of the culture solution included 3.2% polypeptone, 2% yeast extract, 0.5% NaCl, 2% glycerol, 0.05 mL/L Adekanol LG-126 (Asahi Denka Co., Ltd., Tokyo) and 50 μg/mL streptomycin (pH 7.0). To this culture solution, 200 mL of the previous culture solution was inoculated and culture was started at 34° C. In four hours since the beginning of culturing, IPTG (Isopropyl-β-D-thiogalactopyranoside) was added at a rate of 0.2 mM, and culturing was continued further for 20 hours, to obtain the target culture solution. This culture solution was centrifuged by a Sharpless centrifuge, and approximately 800 g of *Pseudomonas putida* transformant was obtained.

*E. coli* bacterium transformant was also cultured under normal aerobic conditions, in 2 L of culture solution. Composition of the culture solution included 3.2% polypeptone, 2% yeast extract, 0.5% NaCl, 2% glycerol, 0.05 mL/L Adekanol LG-126 (Asahi Denka Co., Ltd., Tokyo), 50 μg/mL ampicillin, and 50 μg/mL kanamycin (pH7.0). To this culture solution, 50 mL of the previous culture solution was inoculated and cultured at 30° C. for 29 hours. The culture solution was centrifuged, and approximately 85 g of *E. coli* bacterium transformant was obtained.

Next, the obtained microbe (transformant) was suspended in mM phosphate buffer solution (pH 8), fragmented in a high pressure homogenizer (500 bar). Then, Mydol 12 (Kao Corporation, Tokyo) and KCl were added to achieve the final rates of 1% and 0.1 M respectively, followed by steering for 30 minutes. Next, cell solid was separated and removed by centrifuge (8000×g, 60 minutes at 10° C.), and supernatant liquid was obtained as crude enzyme solution.

In the crude enzyme solutions, *Pseudomonas putida* transformant was found to have a GDH activity of 2930 kU, and a specific activity of 22 U/mg. *E. coli* bacterium transformant was found to have a GDH activity of 259 kU, and a specific activity of 10.3 U/mg.

<Measurement of Glucose Dehydrogenation Activity>

Glucose dehydrogenation activity was measured by tracking a redox reaction of electron acceptor based on glucose dehydrogenation. The electron acceptors were provided by 2,6-dichlorophenol-indophenol (DCIP) and phenazine methosulfate (PMS).

Specifically, 900 μL of 47 mM phosphate buffer solution (pH 6.0) containing 20 mM glucose, 2 mM PMS and 0.1 mM DCIP was placed in a spectrophotometer cell, and was pre-incubated at 37° C. for 3 minutes. Next, 0.5-10 μL of the enzyme solution was added. The cell was immediately turned upside down to begin reaction, and time course monitoring was made for absorption drop at a 600 nm wavelength at 37° C. DCIP has an absorption wavelength of 600 nm and the absorption drop is due to a redox reaction of the electron acceptors based on glucose dehydrogenation.

Here, calculation of the absorbance was made on the basis that DCIP had a mol absorption coefficient of 4.76 mM/cm. A unit (U) of enzyme was defined as an amount by which 1 μM of glucose was oxidized in a minute under the standard measurement conditions. The protein concentration was measured by means of UV method, with a protein concentration defined as being 1 g/L for absorption of 1 at 280 nm.

Example 1

In this Example, the enzyme solution (solubilized GDH fraction) which was obtained from KS1 strain according to the above-described technique was purified by using a combination of hydrophobic chromatography and anion exchange chromatography.

The hydrophobic chromatography was performed by using an Octyl sepharose 4 Fast Flow column (44 mm ID×20 cm Amersham Bioscience KK) which had been equilibrated with 60 mM phosphate buffer solution (pH6). The column was supplied with solubilized GDH fraction (enzyme solution) which was prepared by adding 1 M phosphate buffer solution (pH 6) to achieve the final concentration of 60 mM. Next, 600 mL of 60 mM phosphate buffer solution (pH 6) and 900 mL of 20 mM phosphate buffer solution (pH 8) were passed, and then tightly adsorbed GDH was eluted by supplying eluent. The eluent was provided by 20 mM phosphate buffer solution (pH 8) which contained sodium cholate in dissolved form. The eluent was supplied at a rate of 15 mL/min so that sodium cholate concentration would vary linearly in the range of 0-1 wt %.

As a result, GDH was eluted when the sodium cholate concentration was approximately 0.8 wt %, yielding 340 mL of GDH active fraction. The collected fraction (Octyl collected fraction) had activity readings of 108 U/mg specific activity and 16 kU of total activity.

The anion exchange chromatography was performed by using a Q sepharose Fast Flow column (32 mm ID×12 cm Amersham Bioscience KK) which had been equilibrated with 20 mM phosphate buffer solution (pH 8). To this column, the Octyl collected fraction was supplied, and then eluent was supplied. The eluent was provided by 20 mM phosphate buffer solution (pH 8) which contained 1 wt % sodium cholate. The eluent was supplied at a rate of 8 mL/min and by a volume of 600 mL.

As a result, GDH was eluted specifically when approximately 300 mL of the eluent had been passed, yielding 340 mL of a GDH active fraction. The collected fraction (Q collected fraction) had 770 U/mg specific activity, and 14 kU total activity.

The following Table 2 summarizes the volume of liquid, total activity, specific activity and yield after each operation.

TABLE 2

|  | Liquid Volume | Total Activity | Specific Activity | Yield |
|---|---|---|---|---|
| Solubilized GDH Fraction | 110 mL | 28 kU | 6.8 U/mg | 100% |
| Octhyl Collected Fraction | 340 mL | 16 kU | 108 U/mg | 57% |
| Q Collected fraction | 340 mL | 14 kU | 770 U/mg | 50% |

Example 2

In this Example, the crude enzyme solution obtained from the transformant of *Pseudomonas putida* was purified by using a combination of hydrophobic chromatography and anion exchange chromatography.

In the hydrophobic chromatography, first, a Phenyl cellulofine column (300 mm ID×10 cm, Chisso Corporation, Tokyo) which had been equilibrated with 10 mM phosphate buffer solution (pH 8) containing 0.1 M KCl was supplied with the crude enzyme solution, to let the packing agent hold GDH. Next, 7 L of 10 mM phosphate buffer solution (pH 8) containing 0.1 M KCl, and 21 L of 10 mM phosphate buffer solution (pH 8) were passed. Then, tightly adsorbed GDH was eluted by passing eluent. The eluent was provided by a 20 mm phosphate buffer solution (pH 8) containing sodium cholate in dissolved form. The eluent was supplied at a rate of 7 L/min so that sodium cholate concentration would vary linearly in the range of 0-1 wt %.

As a result, GDH was eluted when the sodium cholate concentration was approximately 0.9 wt %, yielding 7300 mL of an active fraction. The collected fraction (Phenyl collected fraction) had activity readings of 204 U/mg specific activity and 596 kU total activity.

The anion exchange chromatography was performed by using a Q sepharose Fast Flow column (44 mm ID×20 cm Amersham Bioscience KK) which had been equilibrated with 10 mM phosphate buffer solution (pH8). The column was supplied with the Phenyl collected fraction. Note that the phenyl collected fraction was buffer-substituted to 10 mM phosphate buffer solution (pH 8) by using a laboratory module (Asahi Kasei Corporation, Tokyo) which had a 50000 molecular weight cut off, before being supplied to the column. Next, the column was supplied with 600 mL of 10 mM phosphate buffer solution (pH 8), and then with eluent. The eluent was provided by 10 mM phosphate buffer solution (pH 8) containing 1 wt % sodium cholate. The eluent was supplied at a rate of 10 mL/min.

As a result, GDH was eluted specifically when approximately 1400 mL of the eluent had been passed, yielding 313 mL of a GDH active fraction. The collected fraction (Q collected fraction) had 1283 U/mg specific activity, and 390 kU total activity.

The following Table 3 summarizes the volume of liquid, total activity, specific activity and yield after each operation.

TABLE 3

|  | Liquid Volume | Total Activity | Specific Activity | Yield |
|---|---|---|---|---|
| Crude Enzyme Solution | 1950 mL | 2930 kU | 22 U/mg | 100% |
| Phenyl Collected Fraction | 7300 mL | 596 kU | 204 U/mg | 20% |
| Q Collected Fraction | 315 mL | 390 kU | 1283 U/mg | 13% |

Figure 1:
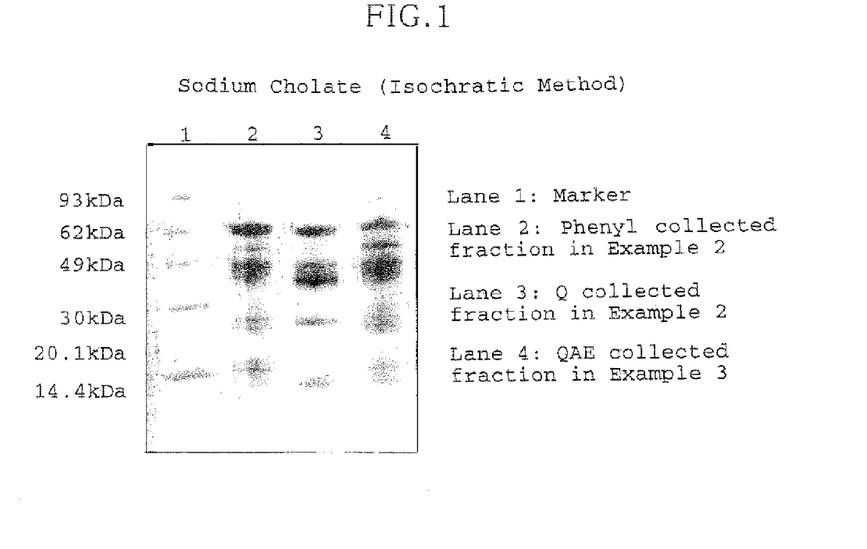
FIG. 1 shows an SDS-PAGE result of an enzyme which was purified with a sodium cholate eluent from a crude enzyme solution obtained from a transformant of *Pseudomonas putida*.

Further, in this Example, the phenyl collected fraction and the Q collected fraction were subjected to electrophoresis, i.e. SDS-PAGE. The SDS-PAGE used Tris-Tricine buffer solution and was performed in polyacrylamide buffer solution in 8-25% gel gradient. Protein which migrated in the gel was stained with CBB. Results of the SDS-PAGE are shown in FIG. 1. In this figure, Lane 2 represents CBB-stained Phenyl collected fraction and Lane 3 represents CBB-stained Q collected fraction.

Example 3

In this Example, the crude enzyme solution obtained from the transformant of *Pseudomonas putida* was purified by using a combination of hydrophobic chromatography and anion exchange chromatography.

The hydrophobic chromatography was performed in the same way as in Example 2. The collected solution was ultra-condensed, to yield 70 mL of phenyl collected fraction, which had a specific activity of 300 U/mg and a total activity of 21 kU.

The anion exchange chromatography was performed by using a QAE-TOYOPEARL 550 column (44 mm ID×10 cm, Tohso Corporation, Tokyo) which had been equilibrated with 10 mM phosphate buffer solution (pH8). The column was supplied with the phenyl collected fraction, and then with eluent. The eluent was provided by 10 mM phosphate buffer solution (pH 8) containing 1 wt % sodium cholate. The eluent was supplied at a rate of 5 mL/min and by a volume of 2000 mL.

As a result, GDH was eluted specifically when approximately 1600 mL of the eluent has been passed, yielding 300 mL of active fraction. The collected fraction (QAE collected fraction) had 1500 U/mg specific activity, and 7.8 kU total activity.

The following Table 4 summarizes the volume of liquid, total activity, specific activity and yield after each operation.

TABLE 4

|  | Liquid Volume | Total Activity | Specific Activity | Yield |
|---|---|---|---|---|
| Crude Enzyme Solution | 420 ml | 80 kU | 59 U/mg | 100% |
| Phenyl Collected Fraction | 70 mL | 21 kU | 300 U/mg | 26% |
| QAE Collected Fraction | 300 mL | 7.8 kU | 1500 U/mg | 10% |

Further, in this Example, the QAE collected fraction was subjected to SDS-PAGE, using the same procedure as used in Example 2, and the protein was stained with CBB. Results of the SDS-PAGE are shown in FIG. 1. In this figure, Lane 4 represents CBB-stained QAE collected fraction.

Comparative Example 1

In this Comparative Example, the crude enzyme solution obtained from the transformant of *Pseudomonas putida* was purified by using a combination of hydrophobic chromatography and anion exchange chromatography.

The hydrophobic chromatography was performed in the same way as in Example 2, yielding 7200 mL of phenyl collected fraction, which had specific activity of 314 U/mg and total activity of 256 kU. In this Comparative Example, however, a portion of the phenyl collected fraction or 1100 mL (Q apply) which represents a total activity of 39 kU was subjected to the following anion exchange chromatography.

The anion exchange chromatography was performed by using a Q sepharose Fast Flow column (44 mm ID×13 cm Amersham Bioscience KK) which had been equilibrated with 10 mM phosphate buffer solution (pH 8). The column was supplied with the Q apply. Thereafter, the column was supplied with 800 mL of 10 mM phosphate buffer solution (pH 8) in order to remove non-adsorbent protein. Then, the column was supplied with eluent. The eluent was provided by 10 mM phosphate buffer solution (pH 8) which contained NaCl in dissolved form. The eluent was supplied at a rate of 7.5 L/min so that NaCl concentration would vary linearly in the range of 0-0.6 M.

As a result, GDH was eluted at two NaCl concentration levels of 0.25 M approx. and 0.4 M approx., yielding 140 mL and 360 mL of active fractions respectively. Each of the active fractions (Q collected fraction (1) and Q collected fraction (2)) were subjected to activity measurement. The Q collected fraction (1) had specific activity of 600 U/mg and total activity of 4.5 kU. The Q collected fraction (2) had specific activity of 432 U/mg and total activity of 12 kU.

The following Table 5 summarizes the volume of liquid, total activity, specific activity and yield after each operation.

TABLE 5

|  | Liquid Volume | Total Activity | Specific Activity | Yield |
| --- | --- | --- | --- | --- |
| Crude Enzyme Solution | 1250 mL | 1066 kU | 36 U/mg | 100% |
| Phenyl Collected Fraction | 7200 mL | 256 kU | 314 U/mg | 24% |
| Q Apply | 1100 mL | 39 kU | 314 U/mg | 24% |
| Q Collected Fraction (1) | 140 mL | 4.5 kU | 600 U/mg | 3% |
| Q Collected Fraction (2) | 360 mL | 12 kU | 432 U/mg | 7% |

Figure 2:
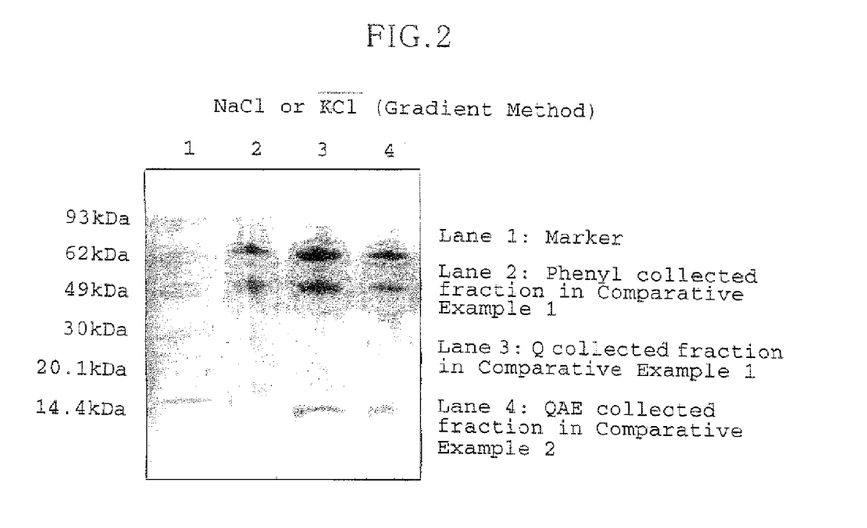
FIG. 2 shows an SDS-PAGE result of an enzyme which was purified with a NaCl or KCl eluent from a crude enzyme solution obtained from the transformant of *Pseudomonas putida*.

Further, in this Comparative Example, the phenyl collected fraction and the Q collected fraction (2) were subjected to SDS-PAGE using the same procedure as used in Example 2, and the protein was stained with CBB. Results of the SDS-PAGE are shown in FIG. 2. In this figure, Lane 2 represents the phenyl collected fraction and Lane 3 represents the Q collected fraction (1).

Comparative Example 2

In this Comparative Example, a portion of the phenyl collected fraction obtained in Comparative Example, or the 2100 mL (QAE apply) which represents the total activity of 74 kU, was subjected to anion exchange chromatography, to obtain purified GDH.

The anion exchange chromatography was performed by using a QAE-TOYOPEARL 550 column (44 mm ID×10 cm Tohso Corporation, Tokyo) which had been equilibrated with 10 mM phosphate buffer solution (pH 8). The column was first supplied with the QAE collected fraction (74 kU total activity). Next, 800 mL of 10 mM phosphate buffer solution (pH 8) was supplied to remove non-adsorbent protein. Then, the column was supplied with eluent. The eluent was provided by 10 mM phosphate buffer solution (pH 8) containing dissolved KCl. The eluent was supplied at a rate of 5 mL/min so that KCl concentration would vary linearly in the range of 0-1M.

As a result, GDH was eluted at two KCl concentration levels of 0.23 M approx. and 0.43 M approx., yielding 200 mL and 400 mL of active fractions respectively. Each of the active fractions (QAE collected fraction (1) and QAE collected fraction (2)) were subjected to activity measurement. The QAE collected fraction (1) had specific activity of 399 U/mg and total activity of 7.5 kU. The QAE collected fraction (2) had specific activity of 217 U/mg and total activity of 6.4 kU.

The following Table 6 summarizes the volume of liquid, total activity, specific activity and yield after each operation.

TABLE 6

|  | Liquid Volume | Total Activity | Specific Activity | Yield |
| --- | --- | --- | --- | --- |
| Crude Enzyme Solution | 1250 mL | 1066 kU | 36 U/mg | 100% |
| Phenyl Collected Fraction | 7200 mL | 256 kU | 314 U/mg | 24% |
| QAE Apply | 2100 mL | 74 kU | 314 U/mg | 24% |
| QAE Collected Fraction (1) | 200 mL | 7.4 kU | 399 U/mg | 2% |
| QAE Collected Fraction (2) | 400 mL | 6.4 kU | 217 U/mg | 2% |

Further, in this Comparative Example, the QAE collected fraction was subjected to SDS-PAGE using the same procedure as used in Example 2, and the protein was stained with CBB. Results of the SDS-PAGE are shown in FIG. 2. In this figure, Lane 4 represents the QAE collected fraction.

Example 4

In this Example, the crude enzyme solution obtained from the transformant of *E. coli* bacterium was purified by using a combination of hydrophobic chromatography and anion exchange chromatography.

The hydrophobic chromatography was performed under the same conditions as in Example 1, using an Octyl sepharose 4 Fast Flow column.

As a result, GDH was eluted at the sodium cholate concentration of approximately 0.8 wt %, yielding 220 mL of GDH active fraction. The collected fraction (Octyl collected fraction) had specific activity of 503 U/mg and total activity of 149 kU.

The anion exchange chromatography was performed by using a Q sepharose Fast Flow column and under the same conditions as in Example 1.

As a result, GDH was eluted specifically when approximately 500 mL of the eluent had been passed, yielding 175 mL of GDH active fraction. The collected fraction (Q collected fraction) had 1147 U/mg specific activity, and 50 kU total activity.

The following Table 7 summarizes the volume of liquid, total activity, specific activity and yield after each operation.

TABLE 7

|  | Liquid Volume | Total Activity | Specific Activity | Yield |
| --- | --- | --- | --- | --- |
| Crude Enzyme Solution | 520 mL | 259 kU | 1 0.3 U/mg | 100% |
| Octhyl Collected Fraction | 220 mL | 149 kU | 503 U/mg | 58% |
| Q Collected Fraction | 175 mL | 50 kU | 1147 U/mg | 19% |

Figure 3:
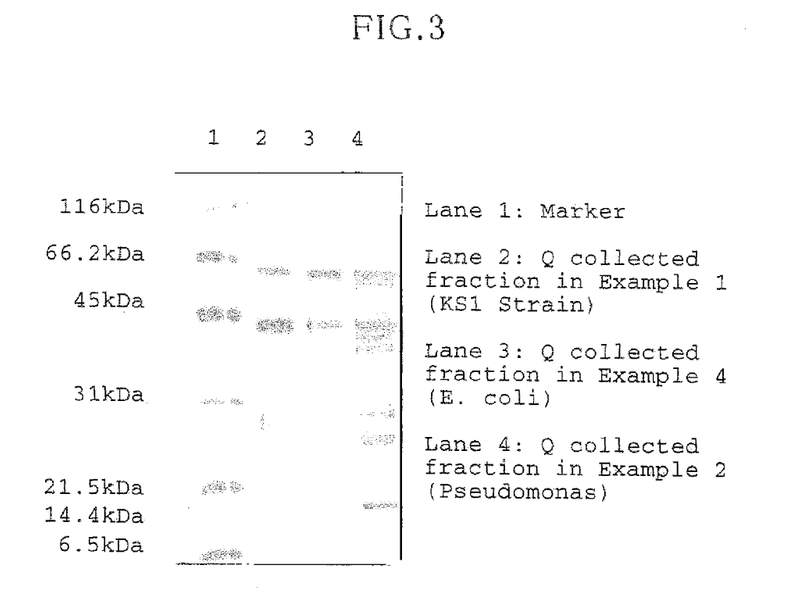
FIG. 3 shows an SDS-PAGE result of an enzyme which was purified with a sodium cholate eluent from a crude enzyme solution obtained from a transformant of *E. coli* bacterium, together with results of two enzymes; one of which was purified from a crude enzyme solution obtained from a transformant of *Pseudomonas putida* while the other was purified from a crude enzyme solution obtained from KS1 strain.

Further, in this Example, the Q collected fraction was subjected to SDS-PAGE using the same procedure as used in Example 2, and the protein was stained with CBB. Results of the SDS-PAGE are shown in FIG. 3. In this figure, Lane 3 represents the Q collected fraction according to the present Example. In FIG. 3, the Q collected fraction (Lane 2) according to Example 1 and the Q collected fraction (Lane 4) according to Example 2 are also subjected to the electrophoresis.

<Discussion on the Results>

As understood from Table 2 through Table 7, GDH has a higher final specific activity and is purified more efficiently when the eluent is provided by cholate (Example 1 through 4) than when the eluent is provided by NaCl or KCl and GDH is purified through gradient elution (Comparative Example 1 and 2). This is also indicated in FIG. 1 and FIG. 2. Specifically, GDH derived from the KS1 strain includes α, β and γ subunits, and their molecular weights in the SDS gel-electrophoretic migration under reducing environment were approximately 60 kDa, 43 kDa and 14 kDa respectively. With this point in mind, FIG. 1 and FIG. 2 will reveal that the collected fractions in Example 2 and Example 3 have wider bands which represent α, β and γ subunits, than the corresponding bands found in the collected fractions in Comparative Examples 1 and 2, while having smaller portions of proteins which have different molecular weights. Therefore, when purifying GDH by using a combination of hydrophobic chromatography and anion exchange chromatography, use of sodium cholate for eluting GDH will lead to efficient purification of GDH.

Further, as understood from FIG. 3, crude enzyme derived from a transformant of host *E. coli* bacterium shows a narrower band for the γ subunit but wider bands for α and β subunits than other crude enzyme solutions. *E. coli* bacterium is advantageous in that it is inexpensive, easily available and has superb self-duplicating capability. Therefore, in terms of industrial application, the method of obtaining a crude enzyme from a transformant hosted by *E. coli* bacterium and purifying this crude enzyme to obtain GDH will be useful.

What is claims is:

1. A method for purifying glucose dehydrogenase using a combination of hydrophobic chromatography and anion exchange chromatography, wherein
the hydrophobic chromatography includes:
a step of causing a stationary phase to hold the glucose dehydrogenase;
a step of eluting unnecessary proteins; and
a step of eluting the glucose dehydrogenase by using an eluent containing a hydroxy-cholate,
the anion exchange chromatography including:
a step of causing a stationary phase to hold the glucose dehydrogenase; and
a step of eluting the glucose dehydrogenase by using an eluent containing a hydroxy-cholate;
wherein the anion exchange chromatography uses an ion-exchange resin containing a quaternary ammonium group as an ion-exchange group;
wherein the glucose dehydrogenase is produced by a microorganism belonging to the genus *Burkholderia*; and
wherein the microorganism belonging to the genus *Burkholderia* is provided by *Burkholderia cepacia* KS1 strain (FERM BP-7306).

2. The method for purifying glucose dehydrogenase according to claim 1, wherein concentration of the hydroxy-cholate in the eluent is varied with time in the hydrophobic chromatography,
concentration of the hydroxy-cholate in the eluent being kept at a constant level in the elution of the glucose dehydrogenase in the anion exchange chromatography.

3. The method for purifying glucose dehydrogenase according to claim 2, wherein the anion exchange chromatography is carried out after the hydrophobic chromatography.

4. The method for purifying glucose dehydrogenase according to claim 1, wherein the hydroxy-cholate is provided by a cholate.

5. The method for purifying protein according to claim 1, wherein the hydroxy-cholate is sodium cholate.

6. The method for purifying protein according to claim 2, wherein the concentration of the hydroxy-cholate in the eluent used in the hydrophobic chromatography is varied in a range of 0-3 wt %.

7. The method for purifying protein according to claim 2, wherein the concentration of the hydroxy-cholate in the eluent used in the anion exchange chromatography is kept constant in a range of 0.5-2.5 wt %.

8. A method for purifying glucose dehydrogenase using a combination of hydrophobic chromatography and anion exchange chromatography; wherein the glucose dehydrogenase includes α-, β- and γ-subunits;
wherein the hydrophobic chromatography includes a step of causing a stationary phase to hold the glucose dehydrogenase, a step of eluting unnecessary proteins, and a step of eluting the glucose dehydrogenase by using an eluent containing a hydroxy-cholate;
wherein the anion exchange chromatography includes a step of causing a stationary phase to hold the glucose dehydrogenase, and a step of eluting the glucose dehydrogenase by using an eluent containing a hydroxy-cholate; and
wherein the anion exchange chromatography uses an ion-exchange resin containing a quaternary ammonium group as an ion-exchange group.

9. The method for purifying glucose dehydrogenase according to claim 8, wherein concentration of the hydroxy-cholate in the eluent is varied with time in the hydrophobic chromatography,
concentration of the hydroxy-cholate in the eluent being kept at a constant level in the elution of the glucose dehydrogenase in the anion exchange chromatography.

10. The method for purifying glucose dehydrogenase according to claim 9, wherein the anion exchange chromatography is carried out after the hydrophobic chromatography.

11. The method for purifying glucose dehydrogenase according to claim 8, wherein the glucose dehydrogenase is produced by a microorganism belonging to the genus *Burkholderia*.

12. The method for purifying glucose dehydrogenase according to claim 11, wherein the microorganism belonging to the genus *Burkholderia* is provided by *Burkholderia cepacia* KS1 strain (FERM BP-7306).

13. The method for purifying glucose dehydrogenase according to claim 8, wherein the glucose dehydrogenase is produced by a transformant,
the transformant being produced by engineering a host microorganism with a DNA from a microorganism belonging to the genus *Burkholderia* for coding the glucose dehydrogenase.

14. The method for purifying glucose dehydrogenase according to claim 13, wherein the host microbe is provided by *Pseudomonas putida*.

15. The method for purifying glucose dehydrogenase according to claim 13, wherein the host microbe is provided by *E. coli* bacterium.

16. The method for purifying glucose dehydrogenase according to claim 1, wherein the eluent used in the anion exchange chromatography also contains a phosphate buffer solution.

17. The method for purifying glucose dehydrogenase according to claim 8, wherein the eluent used in the anion exchange chromatography also contains a phosphate buffer solution.

\* \* \* \* \*